US012558452B2

(12) United States Patent
Taniguchi et al.

(10) Patent No.: US 12,558,452 B2
(45) Date of Patent: Feb. 24, 2026

(54) COATING-SECURING AGENT

(71) Applicant: PUBLIC UNIVERSITY CORPORATION YOKOHAMA CITY UNIVERSITY, Kanagawa (JP)

(72) Inventors: Hideki Taniguchi, Kanagawa (JP); Soichiro Murata, Kanagawa (JP)

(73) Assignee: PUBLIC UNIVERSITY CORPORATION YOKOHAMA CITY UNIVERSITY, Kanagawa (JP)

( * ) Notice: Subject to any disclaimer, the term of this patent is extended or adjusted under 35 U.S.C. 154(b) by 740 days.

(21) Appl. No.: 17/439,938

(22) PCT Filed: Mar. 13, 2020

(86) PCT No.: PCT/JP2020/011144
§ 371 (c)(1),
(2) Date: Sep. 16, 2021

(87) PCT Pub. No.: WO2020/189561
PCT Pub. Date: Sep. 24, 2020

(65) Prior Publication Data
US 2022/0184271 A1 Jun. 16, 2022

(30) Foreign Application Priority Data

Mar. 20, 2019 (JP) ................................. 2019-053047

(51) Int. Cl.
*A61L 24/08* (2006.01)
*C09D 105/04* (2006.01)

(52) U.S. Cl.
CPC ............ *A61L 24/08* (2013.01); *C09D 105/04* (2013.01); *A61L 2300/414* (2013.01)

(58) Field of Classification Search
None
See application file for complete search history.

(56) References Cited

U.S. PATENT DOCUMENTS 5,578,314 A * 11/1996 Cochrum ............ A61L 27/3804
623/23.72
2015/0238307 A1* 8/2015 Galperin .................. A61F 2/142
606/41
2016/0067378 A1* 3/2016 Wagner ................... A61L 24/08
514/23

FOREIGN PATENT DOCUMENTS

| CN | 1897890 | 1/2007 |
| JP | 2012-524739 | 10/2012 |
| JP | 2016-539101 | 12/2016 |
| WO | 98/23226 | 6/1998 |
| WO | 2008/097498 | 8/2008 |
| WO | 2018/073837 | 4/2018 |

OTHER PUBLICATIONS

Kalra A, Wehrle CJ, Tuma F. Anatomy, Abdomen and Pelvis, Peritoneum. [Updated Jul. 25, 2023]. In: StatPearls [Internet]. Treasure Island (FL): StatPearls Publishing; Jan. 2024-, Available from: https://www.ncbi.nlm.nih.gov/books/NBK534788/ (Year: 2023).*
Communication pursuant to Article 94(3) EPC issued Mar. 14, 2024 in corresponding European Patent Application No. 20774456.6.
Capeling, M.M. et al., "Nonadhesive Alginate Hydrogels Support Growth of Pluripotent Stem Cell Derived Intestinal Organoids", Stem Cell Reports, vol. 12, No. 2, (2019), pp. 381-394, XP055978078.
Gu, F et al., "Sustained delivery of vascular endothelial growth factor with alginate beads", Journal of Controlled Release, vol. 96, No. 3, (2004), pp. 463-472, XP004505679.
Extended European Search Report dated Nov. 16, 2022 in corresponding European Patent Application No. 20774456.6.
International Search Report issued Jun. 9, 2020 in International (PCT) Application No. PCT/JP2020/011144.
Yanagi, Yusuke et al., "In vivo and ex vivo methods of growing a liver bud through tissue connection", Scientific Reports, 2017, vol. 7, article No. 14085, pp. 1-15.
English language translation of Office Action issued Feb. 23, 2022 in corresponding Chinese Patent Application No. 202080020657.8.
Sahoo et al., "Alginate and its application to tissue engineering", SN Applied Sciences, 2021, vol. 3, No. 30, 19 pages.
Sarker et al., "Evaluation of Fibroblasts Adhesion and Proliferation on Alginate-Gelatin Cross-linked Hydrogel", PLOS ONE, Sep. 2014, vol. 9. Issue 9, pp. 1-12.

* cited by examiner

*Primary Examiner* — Ali Soroush
*Assistant Examiner* — Afua Bamfoaa Boateng
(74) *Attorney, Agent, or Firm* — Wenderoth, Lind & Ponack, L.L.P.

(57) ABSTRACT

Provided is a coating-fixing agent for transplanting a cell or a tissue onto the surface of an organ, intestinal membrane, peritoneal membrane, etc. Provided are: a formulation for coating and fixing a graft, the formulation comprising alginate; a formulation kit for coating and fixing a graft, comprising a formulation containing alginate and a divalent or higher valent metal salt in combination; and a method for transplanting a graft, comprising: transplanting the graft to a transplant site of a human or a non-human animal, and coating the graft with alginate.

5 Claims, 4 Drawing Sheets
(4 of 4 Drawing Sheet(s) Filed in Color)

(a)

: hEGF (b) Proliferative effect of fetal liver tissue (c) Engraftment of human iPSC liver organoid by Low viscosity sodium alginate + growth factor (a)

Deviation of transplanted tissue
from liver surface and transfer
thereof to another organ 0/22

Engrafted human iPSC liver organoid (b)

COATING-SECURING AGENT

TECHNICAL FIELD

The present invention relates to a coating-fixing agent.

BACKGROUND ART

A previous radical treatment method for organ failure is organ transplantation. Liver transplantation is used as a radical treatment method for liver failure. In liver transplantation, a graft is transplanted to the same location as the harvested liver of a recipient, and anastomosed to the portal vein, the hepatic artery, the hepatic vein, and the bile duct. In hepatocyte transplantation or mesenchymal stem cell transplantation, which has been developed to compensate for the absolute shortage of liver transplantation donors, the cells are administered from the portal vein or the peripheral vein (Non Patent Literatures 1 and 2).

CITATION LIST

Non Patent Literature

Non Patent Literature 1: Treatment of the Crigler-Najjar syndrome type I with hepatocyte transplantation. Fox I J, Chowdhury J R, Kaufman S S, Goertzen T C, Chowdhury N R, Warkentin P I, Dorko K, Sauter B V, Strom S C. N Engl J Med. 1998 May 14; 338 (20): 1422-6.

Non Patent Literature 2: Clinical Hepatocyte Transplantation: What is Next? Squires J E, Soltys K A, McKiernan P, Squires R H, Strom S C, Fox I J, Soto-Gutierrez A. Curr Transplant Rep. 2017 December; 4 (4): 280-289.

SUMMARY OF INVENTION

Technical Problem

The present inventors have devised an approach of detaching a membrane or layer covering a parenchyma organ including liver, and applying a tissue directly thereto, as a totally novel transplantation method. Conventional formulations capable of intraperitoneal coating include oxidized cellulose or hyaluronic acid for preventing adhesive ileus. Although fibrin glue is also used for the purpose of preventing bile spillage or rebleeding from a hepatic resection surface, such a formulation is not used as a coating-fixing agent for tissue transplantation to organ surface.

No coating-fixing agent for transplanted tissues on organ surface has yet been developed. Requirements to be satisfied in applying a tissue to the surface of an organ including the liver include:

1. being less invasive to the transplanted tissue,
2. allowing long-term engraftment of the transplanted tissue, and
3. contributing to the proliferation promotion or maturation of the transplanted tissue.

However, these issues cannot be addressed by conventional techniques.

An object of the present invention is to provide a coating-fixing agent for transplanting a cell or a tissue to the surface of an organ, the mesentery, the peritoneum, etc.

Solution to Problem

The present inventors gelated sodium alginate by addition of a Ca ion; when the gel was used as a coating material, a cell or a tissue could successfully be transplanted to an organ surface and subsequently engrafted, which led to the completion of the present invention. Furthermore, the proliferation of the transplanted tissue was promoted by the addition of a growth factor to sodium alginate.

The present invention is summarized as follows.

(1) A formulation for coating and fixing a graft, the formulation comprising alginate.

(2) The formulation according to (1), wherein the alginate is at least one selected from the group consisting of sodium alginate, potassium alginate, calcium alginate and ammonium alginate.

(3) The formulation according to (1), wherein the formulation is an aqueous solution containing at least one selected from the group consisting of sodium alginate, potassium alginate and ammonium alginate, and the alginate is gelated by the addition of a divalent or higher valent metal ion when in use.

(4) The formulation according to (3), wherein the divalent or higher valent metal ion is a calcium ion.

(5) The formulation according to any of (1) to (4), further comprising a growth factor.

(6) The formulation according to (5), wherein the growth factor is at least one selected from the group consisting of EGF, TGF beta, bFGF, IGF1, EGF, PDGF, NGF, HGF, VEGF and S1P.

(7) The formulation according to any of (1) to (6), wherein the graft is a cell, a cell condensate, a tissue or a combination thereof.

(8) The formulation according to any of (1) to (7) for coating and fixing the graft on the surface of an organ and/or a tissue.

(9) The formulation according to any of (1) to (8), wherein the graft is engrafted onto a transplant site of a human or a non-human animal, an aqueous solution containing the alginate is added dropwise to the graft, and a divalent or higher valent metal ion is further added dropwise to gelate the alginate for coating the graft.

(10) The formulation according to (9), wherein the transplant site is a site from which a membrane or layer covering the tissue and/or the organ of a human or a non-human animal has been detached.

(11) A formulation kit for coating and fixing a graft, comprising a formulation containing alginate and a divalent or higher valent metal salt in combination.

(12) A method for transplanting a graft, comprising: transplanting the graft to a transplant site of a human or a non-human animal, and coating the graft with alginate.

(13) The transplantation method according to (12), wherein the graft is engrafted onto the transplant site of a human or a non-human animal, an aqueous solution containing at least one selected from the group consisting of sodium alginate, potassium alginate and ammonium alginate is added dropwise to the graft, and a divalent or higher valent metal ion is further added dropwise to gelate the alginate for coating the graft.

(14) The method for transplanting a graft according to (12) or (13), wherein the transplant site is a site from which a membrane or layer covering the tissue and/or the organ of a human or a non-human animal has been detached.

Effects of Invention

According to the present invention, a graft can be transplanted to the surface of a tissue and/or an organ.

The present specification encompasses the contents described in the specification and/or drawings of Japanese Patent Application No. 2019-53047 on which the priority of the present application is based.

BRIEF DESCRIPTION OF DRAWINGS

The patent or application file contains at least one drawing executed in color. Copies of this patent or patent application publication with color drawing(s) will be provided by the Office upon request and payment of the necessary fee.

In FIG. 1(*a*), a DPPIV+ rat fetal liver tissue was transplanted to the liver surface of a DPPIV− rat liver cirrhosis model, and coated and fixed using various formulations (sodium alginate, fibrin, oxidized cellulose, and sodium hyaluronate). The figure shows an engrafted tissue at 2 weeks after transplantation.

Upper: macroscopic image of resection plane. Lower: DPPIV-stained tissue image. FIG. 1(*b*) shows an engrafted tissue at 2 weeks after a fetal liver tissue was transplanted to the liver surface of a liver cirrhosis model, and coated and fixed using various formulations (sodium alginate, fibrin, oxidized cellulose, and sodium hyaluronate). FIG. 1(*c*) shows the cross sectional area of the largest resection plane of an engrafted tissue at 2 weeks after a fetal liver tissue was transplanted to the liver surface of a liver cirrhosis model, and coated and fixed using various formulations (sodium alginate, fibrin, oxidized cellulose, and sodium hyaluronate). A proliferation promoting effect was more significantly seen in the group of coating and fixing with sodium alginate than in the other groups. *: $p < 0.05$ vs sodium alginate group. FIG. 1(*d*) shows an immunostained tissue image of a frozen section of an engrafted tissue. In the group having a fetal tissue coated with sodium alginate, a CD31 positive vascular structure was clearly found, and an SE-1 positive sinusoidal structure or HNF4alpha positive hepatocytes were found. FIG. 1(*e*) shows the proportion of a CD31 positive area. A tendency for a higher proportion of the CD31 positive area was seen in the sodium alginate group compared with the other 3 groups. FIG. 1(*f*) shows the proportion of a HNF4alpha positive area. A tendency for a larger number of HNF4alpha positive hepatocytes was seen in the sodium alginate group and the sodium hyaluronate group.

In FIG. 2(*a*), a DPPIV+ rat fetal liver tissue was transplanted to the liver surface of a DPPIV− rat liver cirrhosis model, and coated and fixed using sodium alginate. The figure shows an engrafted tissue at 3 weeks after transplantation. Left: HE stain. Right: DPPIV stain. FIG. 2(*b*) shows a survival rate at 3 weeks after transplantation in which a DPPIV+ rat fetal liver tissue was transplanted to the liver surface of a DPPIV− rat liver cirrhosis model, and coated and fixed using sodium alginate. The survival rate was significantly improved in the transplantation (TP) group compared with a non-transplantation (sham) group. FIG. 2(*c*) shows various blood biochemistry data from transplantation. PLT: platelet, PT: prothrombin time, AST: aspartate aminotransferase, ALT: alanine aminotransferase, ALB: albumin, NH3: ammonia, T-Bil: total bilirubin. *: $p < 0.05$ vs non-transplantation (sham) group.

In FIG. 3(*a*), a gel obtained by reacting sodium alginate with calcium chloride was mixed with human EGF and studied for the sustained release of human EGF to a supernatant (PBS). Low viscosity sodium alginate continually exhibited the sustained release of human EGF. In FIG. 3(*b*), a DPPIV+ rat fetal liver tissue was transplanted to the liver surface of a DPPIV− rat liver cirrhosis model, and 2 weeks later, tissue engraftment was observed. The fetal liver tissue was coated and fixed with low viscosity sodium alginate alone and with low viscosity sodium alginate+ growth factor (bFGF, EGF, NGF, TGF beta, or PDGF), and comparatively studied. The figure shows an engrafted tissue at 2 weeks after transplantation. A proliferation promoting effect on the engrafted tissue was seen in the group supplemented with the growth factor. In FIG. 3(*c*), engraftment was observed as a result of transplanting a human iPS cell-derived liver organoid to the liver surface of an immunodeficient rat liver cirrhosis model. The figure shows macroscopic findings, HE stain, and a human albumin immunostaining image.

In FIG. 4(*a*), engraftment to the liver surface was observed in 22 tested cases without recognizable transfer to non-liver organs when a human iPS cell-derived liver organoid was transplanted to the liver surface of an immunodeficient rat severe liver cirrhosis model using sodium alginate. The figure shows macroscopic findings, HE stain, and immunostaining images of hepatocytes (human albumin) and the bile duct (human CK19). In FIG. 4(*b*), four or eight human iPS cell-derived liver organoids (corresponding to $1 \times 10^6$ hepatocytes per organoid) were transplanted to the liver surface of an immunodeficient rat severe liver cirrhosis model using sodium alginate, and studied for a survival rate improving effect. The eight human iPS cell-derived liver organoids thus transplanted were found to have a marked survival rate improving effect. The figure shows blood biochemistry data at 2 weeks after human iPS cell-derived liver organoid transplantation to the severe liver cirrhosis model. The human iPS cell-derived liver organoid transplantation significantly improved albumin, direct bilirubin, and AST levels.

DESCRIPTION OF EMBODIMENTS

Figure 1:
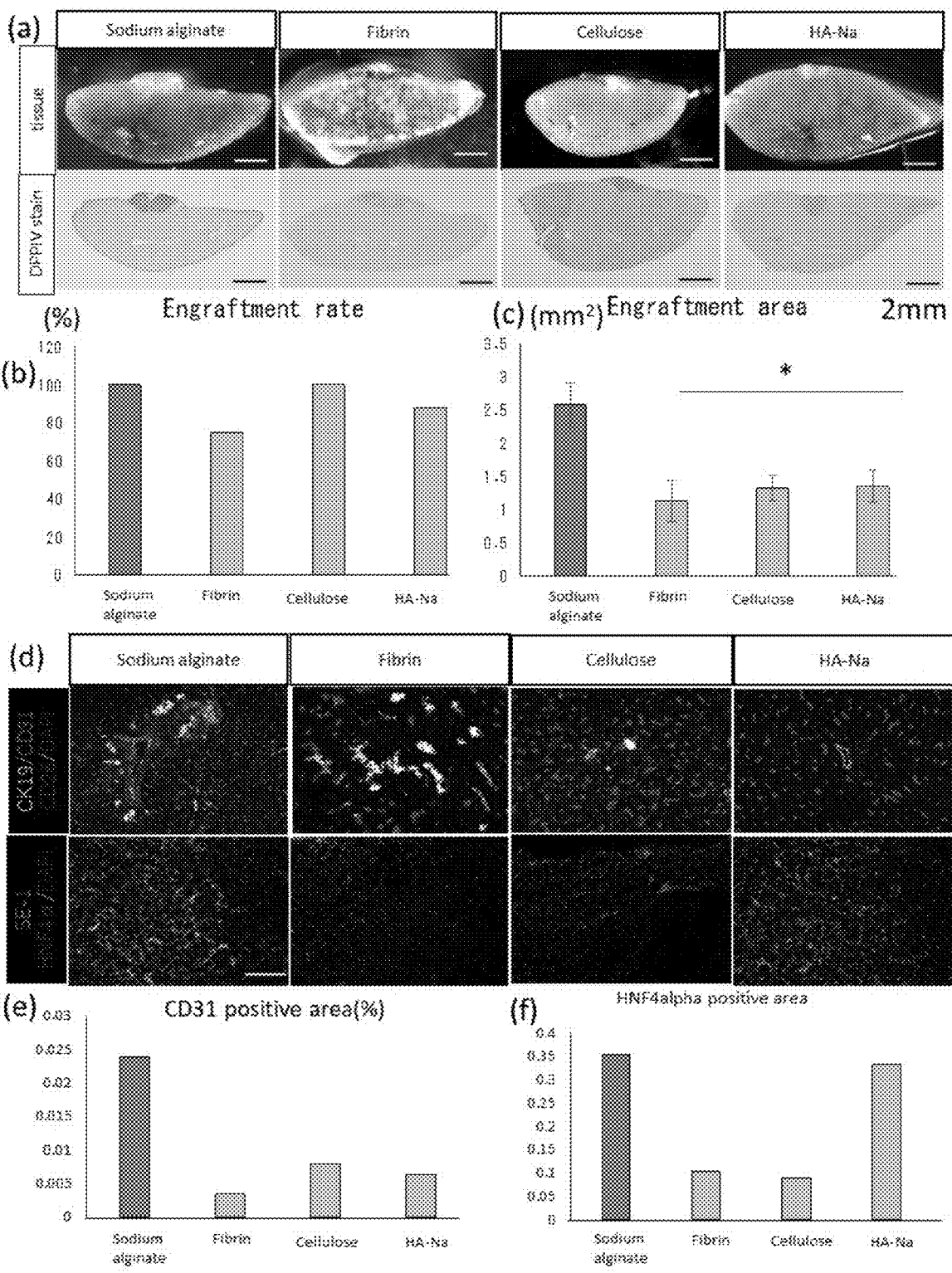
FIG. 1.

Hereinafter, the present invention will be described in detail.

The present invention provides a formulation for coating and fixing a graft, the formulation comprising alginate.

Examples of the alginate can include monovalent metal salts of alginic acid, such as sodium alginate, potassium alginate and ammonium alginate, and divalent metal salts of alginic acid, such as calcium alginate. Among them, a monovalent metal salt of alginic acid is preferred, and sodium alginate is more preferred. Not only one alginate but also a combination of two or more thereof may be used.

Alginic acid is a high molecular weight polysaccharide contained in the alga bodies of brown algae, and is a polymer in which two types of uronic acids, D-mannuronic acid (M) and L-guluronic acid (G), are linearly polymerized. The constituent ratio of the D-mannuronic acid and the L-guluronic acid (M/G ratio) differs depending on the type of the origin alga and also differs depending on a habitat or season even if the organism species is the same. The alginate is a neutral salt in a form in which the carboxyl group of alginic acid is bonded to a metal ion or an ammonium ion. Although alginic acid is insoluble in water, the monovalent metal salt of alginic acid, such as sodium alginate, potassium alginate or ammonium alginate, dissolves well in cold water or hot water to form a viscous aqueous solution. When a divalent or higher valent metal ion (e.g., a calcium ion) is added to the aqueous solution of the monovalent metal salt of alginic acid, such as sodium alginate, potassium alginate or ammonium alginate, ionic cross-linking occurs instantaneously so that the aquation solution is gelated. Mainly, L-guluronic acid (G) of alginic acid is involved in the cross-linking reaction with the divalent or higher valent metal ion. Alginic acid with high ratio of G reacts fast with the divalent or higher valent metal ion, and the formed gel is hard and fragile in nature.

When the formulation is an aqueous solution containing at least one selected from the group consisting of sodium alginate, potassium alginate and ammonium alginate, it is preferred that the alginate be gelated by the addition of a divalent or higher valent metal ion when in use. The gelation forms a covering, which in turn has a long-term tissue fixing power. Examples of the divalent or higher valent metal ion can include magnesium ions, calcium ions, strontium ions, and barium ions. A calcium ion is preferred.

Examples of the aqueous solution of the divalent or higher valent metal ion can include aqueous solutions of metal salts such as calcium chloride, magnesium chloride, calcium sulfate, barium chloride, and strontium chloride.

The ratio between the monovalent metal salt of alginic acid (e.g., sodium alginate, potassium alginate and ammonium alginate) and the divalent or higher valent metal ion (e.g., a calcium ion) is preferably such that 1 mM to 500 mM calcium chloride is in a 0.1 to 4.0% sodium alginate solution, more desirably such that 5 mM to 300 mM calcium chloride is in a 0.3 to 3.0% sodium alginate solution.

The formulation of the present invention may be combined with a divalent or higher valent metal salt (e.g., calcium chloride, magnesium chloride, calcium sulfate, barium chloride and strontium chloride) to form a kit.

The kit may contain a solvent (e.g., purified water, distilled water, ion exchanged water, Milli-Q water, physiological saline and phosphate buffered saline) for preparing a solution of the formulation of the present invention or the divalent or higher valent metal salt, an instrument (e.g., a syringe and an injection needle, a silicone or otherwise mold (which is used to temporarily surround a transplanted tissue at the time of transplantation operation so that alginic acid or calcium chloride will not scatter around and which is removed after the tissue is coated and fixed)) for adding dropwise a solution of the formulation of the present invention or the divalent or higher valent metal salt to a transplant site, an instruction manual, etc.

The monovalent metal salt of alginic acid can have any viscosity ranging from low (20 to 100 mPa·s), medium (100 to 200 mPa·s) to high (400 to 600 mPa·s). Low viscosity is preferred. As shown in the Example to be described later, low viscosity sodium alginate supplemented with a growth factor exhibited the sustained release of the growth factor. The coating and fixing of an engrafted tissue using the low viscosity sodium alginate supplemented with the growth factor promoted proliferation.

The M/G ratio of the monovalent metal salt of alginic acid is preferably on the order of 1.0 to 1.6.

The viscosity of the aqueous alginic acid solution can be measured by a known method using, for example, a rotational viscometer (cone plate type). The known method is, for example, The Japanese Pharmacopoeia Sixteenth Edition, General Tests, Viscosity Determination (cone-flat plate type rotational viscometer). According to The Japanese Pharmacopoeia Sixteenth Edition, General Tests, Viscosity Determination, the viscosity of the monovalent metal salt of alginic acid can be indicated by apparent viscosity when the monovalent metal salt of alginic acid is dissolved in Milli-Q water to prepare a solution having a concentration of 1 w/w %, followed by viscosity measurement using a cone plate type viscometer under such conditions that the measurement temperature is set to 20° C., the cone plate type viscometer is rotated at 1 rpm, and the reading time is set to 2 minutes, with an average value being calculated for the period ranging from 1 minute to 2 minutes after the start.

The formulation of the present invention may further comprise a growth factor. The growth factor is preferably EGF, TGF beta, bFGF, IGF1, EGF, PDGF, NGF, HGF, VEGF, S1P or a combination thereof.

It is desired that medical materials for in vivo use should have a lower endotoxin level than conventional sodium alginate (ALG-Na). ALG-Na used as a base for commercially available medical drugs (oral preparations) or wound dressings is made from alginate that has not been treated for lower endotoxin levels (usually, the endotoxin content is said to range from several tens of thousands to a hundred-odd thousands of EU (endotoxin unit)/g). Such endotoxin-rich, naturally derived ingredient is preferably modified as a material that can be used more safely in vivo. The treatment for lower endotoxin levels can be performed by a known method such as washing, filter-aided filtration, ultrafiltration, purification using a column, adsorption onto a resin or activated carbon, organic solvent treatment or surfactant treatment, or a method equivalent thereto. The endotoxin level can be measured by a known method such as a method using a limulus reagent or a method using Toxinometer.

The method for treatment to reduce the endotoxin level in the alginate contained in the formulation of the present invention is not particularly limited. The endotoxin content is preferably 500 EU/g or less, more preferably 50 EU/g or less, still more preferably 30 EU/g or less, when endotoxin is measured using a limulus reagent. The sodium alginate treated to reduce the endotoxin level is commercially available as Sea Matrix® (Mochida Pharmaceutical Co., Ltd.), etc.

The formulation of the present invention can be in any dosage form such as a liquid preparation, a powder or granules. In the case of a liquid preparation, the solvent can be a pharmaceutically acceptable solvent. Examples thereof can include purified water, distilled water, ion exchanged water, Milli-Q water, physiologically saline and phosphate buffered saline. Such a solvent has preferably been treated to reduce the endotoxin level. When the formulation is a liquid preparation, the concentration of the alginate in the formulation is preferably 0.001 to 10 w/w %, more preferably 0.005 to 8 w/w %, still more preferably 0.01 to 5.0 w/w %. When the formulation of the present invention is a powder or granules, an excipient, a binder, a disintegrant, etc. may be added thereto. When the formulation is a powder or granules, the concentration of the alginate in the formulation is preferably 0.1 to 100 w/w %, more preferably 1 to 80 w/w %, still more preferably 10 to 50 w/w %. When the formulation is a powder or granules, a solvent such as water is preferably added to the formulation before it is used as a solution.

The formulation of the present invention may be supplemented with other pharmaceutically acceptable additives such as a dissolution aid, a solubilizer, an emulsifier, a dispersant, an antioxidant, a preservative and a light blocking agent.

The formulation of the present invention can be used for coating and fixing a graft on the surface of an organ and/or a tissue.

The organ refers to a part within the intraperitoneal space and also includes lung, heart, and blood vessels. Examples of the organ can include liver, bile duct, intestines, pancreas, kidney, heart, lung, blood vessels and trachea.

The tissue refers to a structure in which one type or two or more types of cells are aggregated in a given pattern. Examples of such tissue can include connective tissues (the skin, the tendon, the cartilage, the bone, etc.), muscular tissues, and nerve tissues (central nerve such as brain and spinal cord, peripheral nerve, etc.).

Examples of the graft can include cells, cell condensates, tissues, and combinations thereof.

The cell to be transplanted can be a cell that is expected to display functions by being transplanted to a living body. Examples of such cell can include functional cells that constitute organs or tissues, and undifferentiated cells that differentiate into functional cells. Examples of the undifferentiated organ or tissue cell can include: functional cells that constitute ectodermal parts such as brain, spinal cord, adrenal medulla, epidermis, hair/nail/cutaneous glands, sensory organs, peripheral nerve and lens, and cells capable of differentiating into these parts; functional cells that constitute mesodermal parts such as kidney, ureter, heart, blood, gonad, adrenal cortex, muscle, skeletal frame, dermis, connective tissues and mesothelium, and cells capable of differentiating into these parts; and functional cells that constitute endodermal parts such as liver, pancreas, intestines, lung, thyroid, parathyroid and urinary tract, and cells capable of differentiating into these parts. Among terms used by those skilled in the art, hepatoblast, hepatic progenitor cells, pancreatoblast, hepatic precursor cells, pancreatoblast, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cell, cardiac mesoderm, cardiovascular progenitor cells, cardiac progenitor cells (J R. Spence, et al., Nature.; 470 (7332): 105-9. (2011); Self, et al., EMBO J.; 25 (21): 5214-5228. (2006); J. Zhang, et al., Circulation Research.; 104: e30-e41 (2009); and G. Lee, et al., Nature Biotechnology 25, 1468-1475 (2007)), etc. are included in the undifferentiated organ or tissue cell. The undifferentiated organ or tissue cell can be prepared according to a known method from pluripotent stem cells such as induced pluripotent stem cells (iPS cells) or embryonic stem cells (ES cells). The cell may be derived from an organ or a tissue or may be derived from cancer. A cancer model animal can be prepared by transplanting cancer cells to a non-human animal.

The cell condensate to be transplanted may be any condensate of cells, such as an organoid, a spheroid, a cell aggregate, or a cell sphere, and may comprise one type of cell or may comprise two or more types of cells. The "organoid" is a structure that can differentiate into an organ by maturation. As one example, WO2013/047639 discloses a method for preparing an organoid from three types of cells, i.e., organ or tissue cells (progenitor or precursor cells), vascular cells (preferably vascular endothelial cells), and undifferentiated mesenchymal cells or cells differentiated therefrom. By using the formulation of the present invention, an organoid prepared by the above-described method could advantageously be transplanted to and engrafted in a living body (the Example to be described later).

The tissue to be transplanted may be a tissue separated from an individual (e.g., the whole or a portion of tissues that constitute a part such as an organ); alternatively, it may be a tissue induced from functional cells that constitute an organ or a tissue, or undifferentiated cells or pluripotent cells that differentiate into functional cells. By using the formulation of the present invention, a tissue derived from a living body could advantageously be transplanted into and engrafted in a living body (the Example to be described later).

The formulation of the present invention was found to have a proliferation promoting effect on transplanted tissues, as compared with fibrin glue, oxidized cellulose and sodium hyaluronate.

The formulation of the present invention can be used in such an embodiment that the graft is engrafted onto a transplant site of a human or a non-human animal, an aqueous solution containing alginate is added dropwise to the graft, and a divalent or higher valent metal ion is further added dropwise to gelate the alginate for coating the graft. The transplant site is preferably a site from which a membrane or layer covering the tissue and/or the organ of a human or a non-human animal has been detached.

The present invention also provides a method for transplanting a graft, comprising: transplanting the graft to a transplant site of a human or a non-human animal, and coating the graft with alginate. For example, the graft may be engrafted onto the transplant site of a human or a non-human animal, an aqueous solution containing at least one selected from the group consisting of sodium alginate, potassium alginate and ammonium alginate is added dropwise to the graft, and a divalent or higher valent metal ion is further added dropwise to gelate the alginate for coating the graft. The transplant site is preferably a site from which a membrane or layer covering the tissue and/or the organ of a human or a non-human animal has been detached.

Examples of the non-human animal can include mice, rats, rabbits, pigs, dogs, monkeys, cattle, horses, sheep and chickens.

Examples of the membrane or layer covering a tissue and/or an organ can include intestinal membrane, peritoneal membrane, cranial pia mater, fascia, epicardium, visceral pleura, intestinal serosa, hepatic membrane and renal membrane.

The detachment of the membrane or layer can be performed using an injection needle, an electrosurgical knife, a bipolar electrosurgical knife, a surgical knife, Cavitron ultrasonic surgical aspirator (CUSA) or the like.

The amount of the alginate to be used is preferably 0.1 to 100 mg, more preferably 1 to 10 mg, still more preferably 2 to 5 mg, per $cm^2$ of the transplant site.

The dropwise addition of the alginate and the divalent or higher valent metal ion can be performed using an injector, a dropper, a sprayer or the like.

The formulation and the transplantation method of the present invention can find various applications such as tissue transplantation to liver surface intended for liver cirrhosis treatment, a method for treating chronic hepatitis such as non-alcoholic steatohepatitis or alcoholic hepatitis, and regenerative medicine targeting lung, kidney, pancreas and other organs or tissues.

EXAMPLES

Hereinafter the present invention will be described in more detail with reference to Example.

Example 1

Experimental Method
Coating Agent for Transplantation

The coating agents used for transplantation were as follows: sodium alginate (Sea Matrix from Mochida Pharmaceutical Co., Ltd. was diluted to 1% for use; AL20/viscosity was 20 to 100 mPa·s, AL100/viscosity was 100 to 200 mPa·s, AL500/viscosity was 400 to 600 mPa·s); Matrigel (Corning Inc.); fibrinogen (Sigma-Aldrich Co., LLC, F8630); thrombin (Sigma-Aldrich Co. LLC, T7513), with fibrinogen and thrombin being freshly mixed at 100:1 before use to prepare fibrin; oxidized cellulose (Johnson & Johnson K.K.); and sodium hyaluronate (Kaken Pharmaceutical Co., Ltd.) The sodium alginate was added onto a tissue and then gelated by the dropwise addition of a solution of calcium chloride (Nacalai Tesque, Inc.; diluted to 10% with distilled water).

Growth Factor bFGF(Sigma B5887 0.1 pg/ml), EGF (Sigma E9644 1 ng/ml), NGF (Sigma N1408 0.2 ng/ml), IGF-1(Sigma 13769 15 ng/ml), TGFbeta (Sigma H8541 2.5 µg/ml), PDGF (Sigma P3201 12 pg/ml).

Preparation of Liver Cirrhosis Model Rat

Three week old DPP4– F344 rats (Charles River Laboratories Japan, Inc., Kanagawa, Japan) were acclimated for 2 weeks. These rats were given intraperitoneal injection of N-nitrosodimethylamine (FUJIFILM Wako Pure Chemical Corp.) (DMN) at 10 mg/kg (body weight) concentration for 3 consecutive days/week. The IL2rg KO F344 rats used were provided by Kyoto University.

Method for Preparing Fetal Liver Tissue

The liver tissues used were collected from the ED14 fetus of a DPPIV+ F344 rat (Japan SLC, Inc., Shizuoka, Japan).

Transplantation Method

After blocking the portal blood flow of each rat using vascular clamp forceps, the middle lobe surface was sharpened by using an 18 G needle (Terumo corp.). After detachment, compression hemostasis was performed using a cotton swab. The ED14 fetal liver tissue was transplanted onto the DPP4– F344 rat model's cirrhotic liver surface and overlaid with each coating agent. The vascular clamp forceps were removed, followed by the closure of the abdominal cavity. The liver was harvested 14 days after transplantation, and engrafted tissues were comparatively studied.

DPPIV Staining

Frozen tissue sections were fixed with a solution containing a mixture of acetone (FUJIFILM Wako Pure Chemical Corp.) and chloroform (FUJIFILM Wako Pure Chemical Corp.) in equal amounts. Then, these sections underwent enzymatic histochemical staining at ordinary temperature for 20 minutes using a staining solution. The staining solution consisted of 1 mg/mL of Fast Blue BB Salt hemi (zinc chloride) salt (Sigma-Aldrich Co. LLC) in 1 mL of 1× PBS and 8 mg/mL of Gly-Pro 4-methoxy-P-naphthylamide hydrochloride (Sigma-Aldrich Co. LLC) in 1 mL of dimethyl sulfoxide (FUJIFILM Wako Pure Chemical Corp.), which were mixed at a ratio of 20:1 individually. The sections thus stained were soaked for 5 mitutes, for dye fixation, in a 2% copper sulfate aqueous solution prepared by dissolving copper(II) sulfate pentahydrate (FUJIFILM Wako Pure Chemical Corp.) in Milli-Q water. Then, the cells were immersed in 10% formalin for 10 minutes for tissue fixation, followed by replacement with Milli-Q water. Then, 10 min staining with Carrazi's hematoxylin (Muto Pure Chemicals Co., Ltd.) was performed. After rinsing with tap water, the slides were washed for 30 minutes under running tap water to remove excess stain. Finally, Apaci mounting agent (FUJIFILM Wako Pure Chemical Corp.) was added dropwise, and a glass slide (Matsunami Glass Ind., Ltd.) was placed and sealed.

Immunostaining

Frozen tissue sections were fixed with a solution containing a mixture of acetone (FUJIFILM Wako Pure Chemical Corp.) and methanol (FUJIFILM Wako Pure Chemical Corp.) in equal amounts. After air-drying, the dyed sample was surrounded by a water repellent pen (Dako). After the water repellent treatment, permeabilization was performed thrice using 0.05% PBS with Tween 20 (PBST) for 10 minutes. Next, blocking was performed at room temperature for 1 hour using Blocking One (Nacalai Tesque, Inc.). Thereafter, a primary antibody solution diluted to an appropriate concentration with Blocking One was placed over and reacted at 4° C. overnight. After the reaction, the slide was washed thrice with PBST for 10 minutes. Then, a secondary antibody solution appropriately diluted with Blocking One was placed over and reacted at room temperature for 1 hour. After washing with PBS for 10 minutes, a mixture of DAPI (4',6-diamidino-2-phenylindole dihydrochloride, Invitrogen Corp.) and Apaci mounting agent (FUJIFILM Wako Pure Chemical Corp) at 1:1000 was added dropwise, covered with a glass slide (Matsunami Glass Ind., Ltd.) and then sealed.

The antibodies used are as follows.

Primary Antibody

Anti-Rat CD26 (BD Bioscience, 559639)
Anti-Rat CD31 (BD Bioscience, 550300)
Anti-Keratin CK19 (Progen Biotechnik GmbH, 61029)
Anti-Rat Hepatic Sinusoid Endothelial Cell (SE-1) (Immuno-Biological Laboratories, 10078)
Anti-HNF4a (H-1) (Santa Cruz, sc-374229)
Anti-human Albumin (Sigma)
Anti-human nuclei (Merck MAB1281)

Prothrombin Time Measurement

Blood collected from the animals used in the experiment was subjected to measurement using CoaguChek(R) XS (F. Hoffmann-La Roche, Ltd.).

Blood Count Examination

Blood collected from the animals used in the experiment was subjected to anticoagulation treatment with EDTA, then to measurement using fully automatic blood cell counter MEK-6550 Celltac a (Nihon Kohden Corp.).

Blood Biochemistry Examination

Blood collected from the animals used in the experiment was centrifuged at 4000 rpm for 20 minutes to recover serum. The recovered serum was analyzed for AST (aspartate aminotransferase), ALT (alanine aminotransferase), NH3 (ammonia), ALB (albumin) and T-Bil (total bilirubin) using FUJI DRI-CHEM Slide (FUJIFILM Corp.) The measurement employed DRI-CHEM 7000V (FUJIFILM Corp.)

Method for Measuring Hyaluronic Acid

Rat serum was collected and subjected to measurement using hyaluronic acid ELISA kit (DuoSet, Invitrogen Corp.).

Method for Preparing Human iPSC Liver Organoid (1) Preparation of Hepatic Endodermal Cells (HEs)

As for HEs, human iPS cell-derived hepatic endodermal cells (Cell Reports 21, 2661-2670, 2017) or PXB cells (PhoenixBio Co., Ltd.) were used. The medium used was a 1:1 mixture of GM BulletKit (manufactured by Lonza Group AG) and HCM BulletKit (manufactured by Lonza Group AG) from which hEGF (recombinant human epithelial cell growth factor) had been removed; the mixture was then supplemented with dexamethasone and oncostatin M.

(2) Preparation of Mesenchymal Cells (MCs)

As for MCs, cells separated from human bone marrow (Lonza, cat. No. PT-2501), cells separated from human umbilical interstitium (Wharton's duct) or human iPS cell-derived mesenchymal cells (Cell Reports 21, 2661-2670, 2017) were used. Mesenchymal stem cells (hMSCs) separated from human bone marrow, which were mainly used in this experiment, were cultured using a dedicated medium (MSCGM2™ ®) (Promocell C-28009) prepared for hMSC culture.

(3) Preparation of Vascular Cells (ECs)

As for ECs, human iPS cell-derived vascular endothelial cells (Cell Reports 21, 2661-2670, 2017) or normal umbilical vein endothelial cells (HUVEC) were used. The HUVEC used was cells that were either separated from the umbilical cord kindly provided at the time of delivery by a pregnant woman with informed consent or purchased (HUVECs (Lonza, cat. No. 191027), etc.), and cultured through 5 or less passages using EGM® BulletKit® (Lonza CC-4133).

(4) Three-Cell Condensate

Matrigel coating was performed: undiluted Corning® Matrigel® or a solution containing a mixture of Matrigel and a medium at a ratio of 1:1 was placed at 300 μl/well and left standing for 10 minutes or longer in an incubator of 37° C. and 5% CO2 until hardening occurred. $5 \times 10^5$ cells of iPS cell-derived hepatic endodermal cells or human adult hepatocytes, $3.5 \times 10^5$ cells of human iPS cell-derived vascular cells or human umbilical vein-derived vascular endothelial cells, and $1 \times 10^4$ cells of human iPS cell-derived mesenchymal cells or human mesenchymal cells were mixed in a 24-well plate(the respective cell counts refer to the number per well), and then cultured for 2 days in an incubator of 37° C. The three-cell condensate may be prepared using a micropatterned plate.

Results

Study on optimum coating agent for fetal liver tissue transplantation to rat liver surface Fetal liver tissues were transplanted to the surface of the rat liver presenting with liver cirrhosis 2 weeks after N-nitrosodimethylamine (FUJIFILM Wako Pure Chemical Corp.) (DMN) administration, and separately coated and fixed with sodium alginate, fibrin, oxidized cellulose and sodium hyaluronate (FIG. 1a). As a result of confirming the engraftment of the transplanted tissues by DPPIV staining, an engraftment rate of 70% or more was confirmed by all the coating agents (FIG. 1b). As a result of comparing the largest resection areas of the engrafted tissues for these coating agents, the area with sodium alginate was confirmed to be significantly high among the four coating agents (FIG. 1c).

In order to examine the state of formation of a vasculature in the engrafted tissues and the degree of maturation of liver tissues, immunohistochemical staining was performed, and the expression of an engrafted tissue marker CD26, a vascular endothelial cell marker CD31, a bile duct endothelial cell marker CK19, a hepatocyte marker HNF4a and a sinusoidal endothelial cell marker SE-1 was studied (FIG. 1d). As a result, a significantly higher proportion of a CD31-positive site in the engrafted tissues was confirmed for sodium alginate than for the other 3 coating agents (FIG. 1e). The HNF4α-positive rate of the engrafted tissues was significantly higher for sodium alginate and sodium hyaluronate than for the other clinically applicable coating agents (FIG. 1f).

Figure 2:
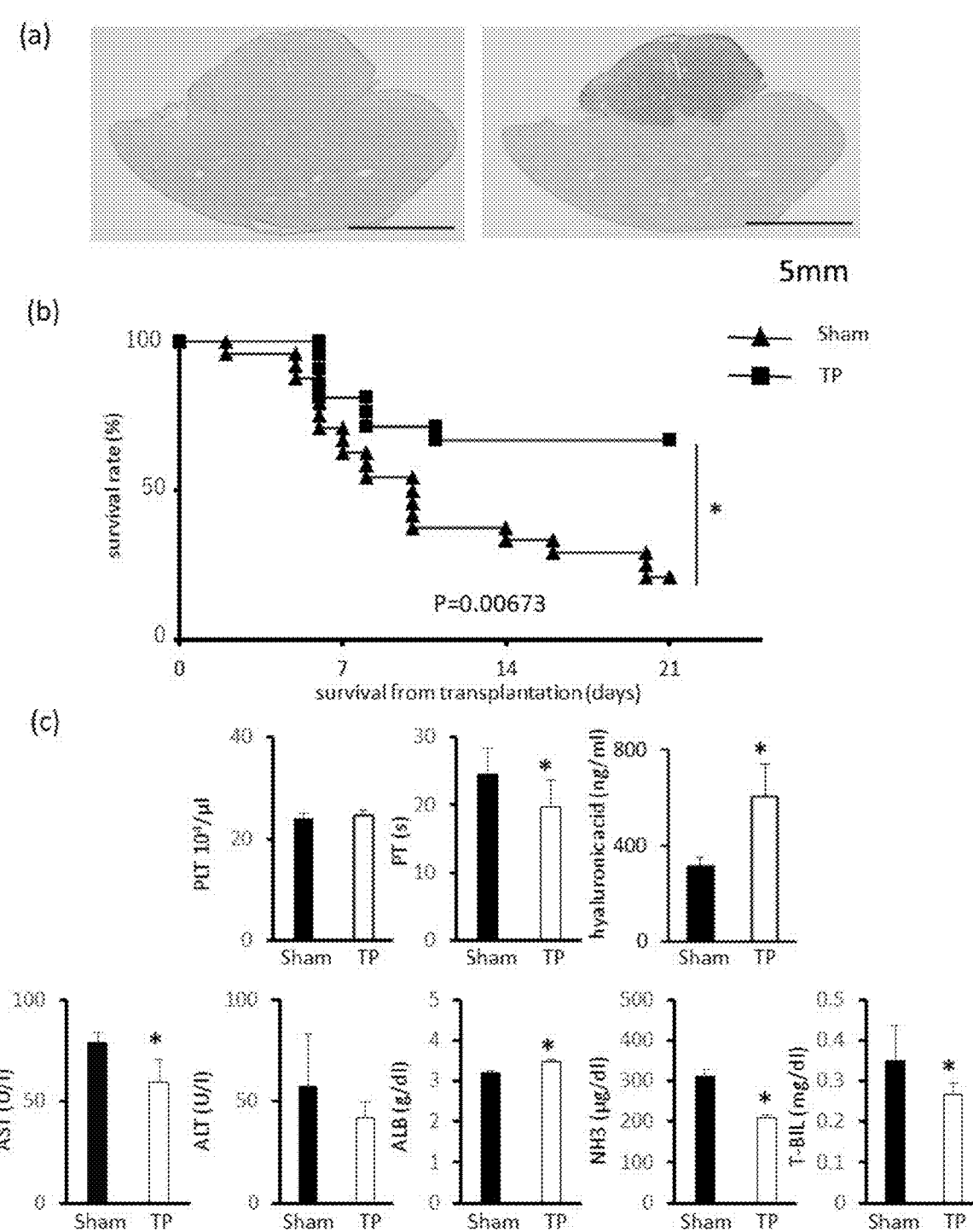
FIG. 2.

Study on therapeutic effect in fetal tissue transplantation to rat liver surface A therapeutic effect brought about by rat fetal liver transplantation to liver surface in a rat decompensated liver cirrhosis model was studied. As a result, the engraftment of transplanted tissues, the construction of a vasculature, and the maturation of liver tissues were confirmed in rat fetal liver tissue transplantation to liver surface with sodium alginate coating (FIG. 2a). Comparative study with a sham operation group (only the detachment operation of the hepatic membrane was carried out) demonstrated that survival rates in rat fetal liver tissue transplantation to liver surface were improved (FIG. 2b). As a result of conducting blood biochemistry examination, improvement in liver function markers AST and ALT was seen 1 week after transplantation. There were also found improved levels of Child-Pugh classification related markers T-Bil and NH3, a shortened prothrombin time, and significantly improved levels of serum ALB and serum hyaluronic acid at 1 week after transplantation (FIG. 2c).

Figure 3:
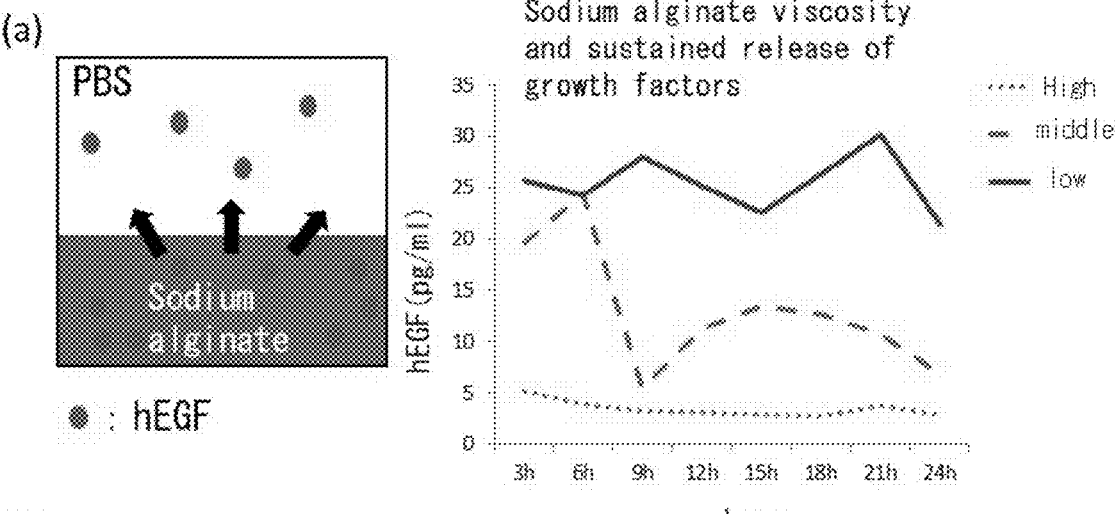
FIG. 3.
Figure 3:
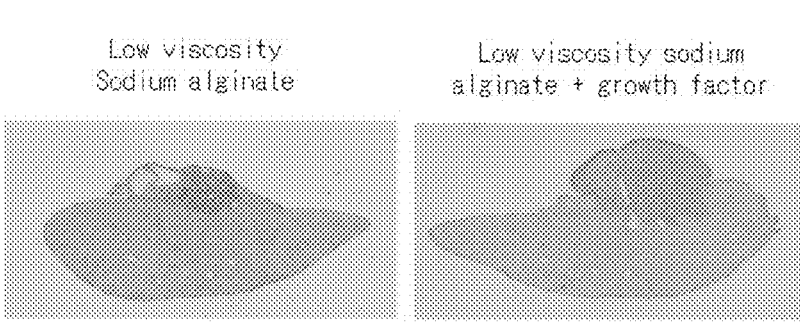
Figure 3:
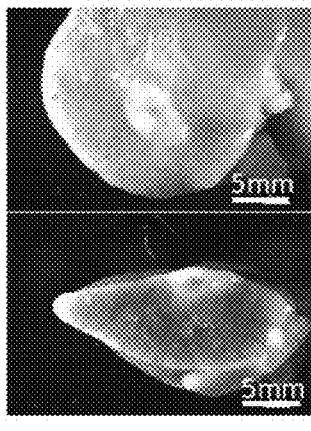
Figure 3:
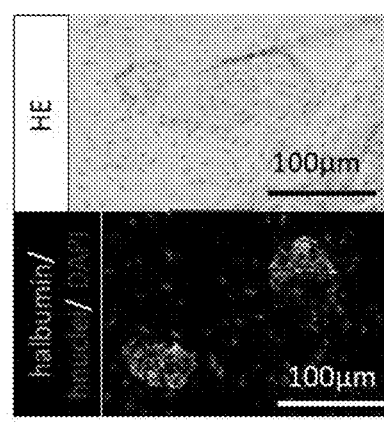
Figure 4:
FIG. 4.
Figure 4:
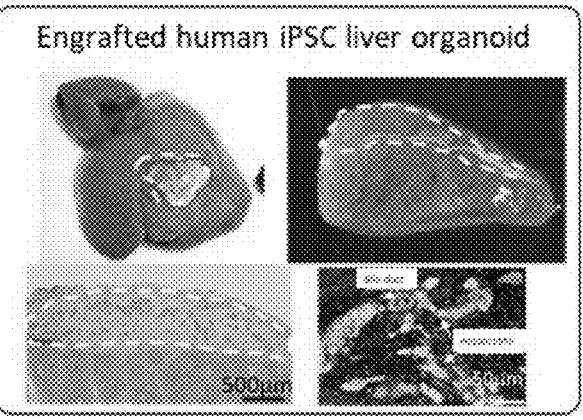
Figure 4:
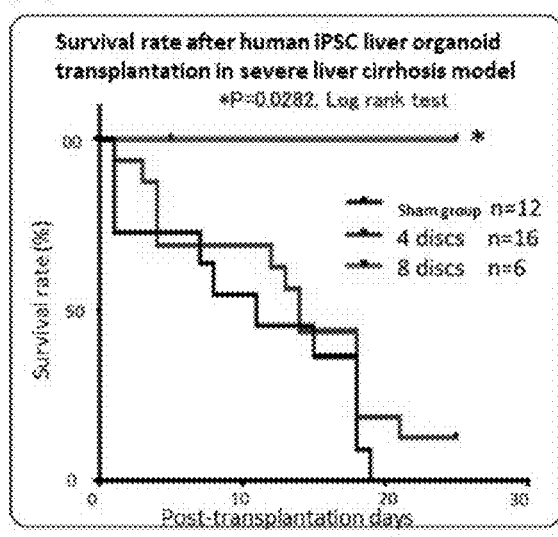
Figure 4:
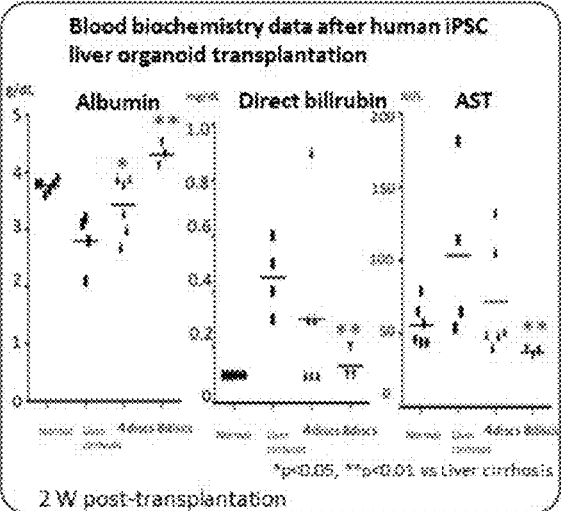

In order to study sustained release by sodium alginate, human EGF was added to high viscosity, medium viscosity or low viscosity sodium alginate, which was then gelated with calcium chloride. When the sustained release of human EGF to neighboring PBS was studied, the low viscosity sodium alginate exhibited the highest release of EGF to the neighborhood (FIG. 3a). Fetal liver tissues were transplanted to the surface of a cirrhotic liver and coated with low viscosity sodium alginate. In this operation, the addition of growth factors (EGF, TGF beta, bFGF, IGF1, EGF, PDGF, and NGF) contained in Matrigel increased the area of engrafted tissues (FIG. 3b). Engraftment of a human iPS cell-derived three-cell condensate was also found on the surface of the cirrhotic liver when the coating-fixing agent containing low viscosity sodium alginate supplemented with a growth factor was used (FIG. 3c).

Discussion

The tissue transplantation method used in this study is an approach by which tissues larger in size than cells for use in transportal transplantation which is performed as conventional cell therapy can be orthotopically engrafted to the liver. Hence, this method may presumably contribute to solving the problem with transportal transplantation, i.e., the small number of transplanted cells. Use of sodium alginate supplemented with growth factors (bFGF, EGF, IGF-1, PDGF, NGF, and TGF beta) contained in Matrigel is capable of further enhancing the proliferative performance of transplanted tissues.

The novel coating-fixing agent according to the present invention is drastically improved over conventional techniques in terms of:

1. being less invasive to the transplanted tissue,
2. allowing long-term engraftment of the transplanted tissue, and
3. contributing to the proliferation promotion or maturation of the transplanted tissue.

Furthermore, low viscosity sodium alginate supplemented with an optional growth factor can contribute to further proliferation promotion of the transplanted tissue.

All publications, patents and patent applications cited herein are incorporated herein by reference in their entirety.

INDUSTRIAL APPLICABILITY

The present invention can be used in the transplantation of a cell, a cell condensate or a tissue to a living body.

The invention claimed is:

1. A method for transplanting a graft onto an organ surface, comprising:

(a) detaching a membrane or layer covering the organ surface at a transplant site of a human or a non-human animal, (b) transplanting the graft to the transplant site on the organ surface of (a), wherein the graft contacts directly with the organ surface, and (c) coating the graft of (b) with a gel formed with alginate and a divalent or higher valent metal ion, thereby fixing the graft onto the transplant site after the graft has been transplanted onto the organ surface.

2. The method for transplanting a graft according to claim 1, wherein the alginate is at least one selected from the group consisting of sodium alginate, potassium alginate and ammonium alginate.

3. The method according to claim 1, wherein the graft is a cell, a cell condensate, a tissue or a combination thereof.

4. The method according to claim 1, wherein the divalent or higher valent metal ion is a calcium ion.

5. A method for transplanting a graft onto an organ surface, comprising: after transplanting the graft to a transplant site on an organ surface of a human or a non-human animal, adding dropwise to the graft an aqueous solution containing at least one selected from the group consisting of sodium alginate, potassium alginate and ammonium alginate, and further adding dropwise a divalent or higher valent metal ion to gelate the alginate for coating the graft, wherein the graft contacts directly the organ surface.

\* \* \* \* \*